United States Patent
Ebihara et al.

(10) Patent No.: US 10,400,086 B2
(45) Date of Patent: Sep. 3, 2019

(54) THERMAL EXPANDABILITY ADJUSTER, USE AS THERMAL EXPANDABILITY ADJUSTER, THERMOSET RESIN COMPOSITION, INSULATING MATERIAL, SEALING MATERIAL AND CONDUCTIVE PASTE EACH CONTAINING THERMOSET RESIN COMPOSITION, CURED PRODUCTS, PREPREG AND MEMBER OBTAINED BY CURING THERMOSET RESIN COMPOSITION OF PREPREG, METHOD OF ADJUSTING THERMAL EXPANSION RATE, AND MEMBER MANUFACTURED USING METHOD OF ADJUSTING

(71) Applicant: AIR WATER INC., Hokkaido (JP)

(72) Inventors: Yousuke Ebihara, Ibaraki (JP); Osamu Koyama, Ibaraki (JP)

(73) Assignee: AIR WATER INC., Hokkaido (JP)

( * ) Notice: Subject to any disclaimer, the term of this patent is extended or adjusted under 35 U.S.C. 154(b) by 14 days.

(21) Appl. No.: 15/550,289

(22) PCT Filed: Jan. 28, 2016

(86) PCT No.: PCT/JP2016/052422
§ 371 (c)(1),
(2) Date: Aug. 10, 2017

(87) PCT Pub. No.: WO2016/139989
PCT Pub. Date: Sep. 9, 2016

(65) Prior Publication Data
US 2018/0030242 A1 Feb. 1, 2018

(30) Foreign Application Priority Data
Mar. 4, 2015 (JP) .................................. 2015-043020

(51) Int. Cl.
*C08G 59/32* (2006.01)
*C08G 59/40* (2006.01)
*C08G 59/62* (2006.01)
*C08K 5/3445* (2006.01)
*C08J 5/24* (2006.01)
*C08G 59/26* (2006.01)
*H01L 23/14* (2006.01)
*C07D 487/04* (2006.01)
(Continued)

(52) U.S. Cl.
CPC .......... *C08K 5/3445* (2013.01); *C07D 487/04* (2013.01); *C08G 59/26* (2013.01); *C08G 59/32* (2013.01); *C08J 5/18* (2013.01); *C08J 5/24* (2013.01); *H01L 23/14* (2013.01); *H01L 23/293* (2013.01); *H05K 1/0271* (2013.01); *H05K 1/0346* (2013.01); *H05K 1/0373* (2013.01); *C08J 2300/24* (2013.01); *C08J 2363/00* (2013.01); *H01B 1/20* (2013.01);

*H01L 23/295* (2013.01); *H05K 1/095* (2013.01); *H05K 2201/068* (2013.01)

(58) Field of Classification Search
CPC .............. C08K 5/3445; C08G 2190/00; C08G 59/3245; C08G 59/4042; C08G 59/621
See application file for complete search history.

(56) References Cited

U.S. PATENT DOCUMENTS

| 4,379,909 A | 4/1983 | Falkenburg et al. |
| 10,000,622 B2 * | 6/2018 | Kumano .................. C08L 47/00 |
| 2016/0297951 A1 | 10/2016 | Kumano et al. |

FOREIGN PATENT DOCUMENTS

| CN | 105745213 A | 7/2016 | |
| DE | 1932305 A1 * | 2/1966 | ............. C08G 30/10 |

(Continued)

OTHER PUBLICATIONS

Computer-generated English-language translation of JP2015-120885 A.*

(Continued)

*Primary Examiner* — Vu A Nguyen
(74) *Attorney, Agent, or Firm* — Hamre, Schumann, Mueller & Larson, P.C.

(57) ABSTRACT

A thermal expandability adjuster is provided which contains a glycoluril derivative compound represented by formula (1) below. The thermal expandability adjuster can reduce the linear thermal expansion coefficient of a cured product of a thermoset resin composition used for an insulating resin layer or the like and is effective for suppressing deformation of a circuit substrate due to heating. Compounding the above thermal expandability adjuster can reduce the linear thermal expansion coefficient of a cured product obtained by curing a thermoset resin composition and it is therefore possible to provide a member that exhibits small deformation due to heat.

[Chemical Formula 1]

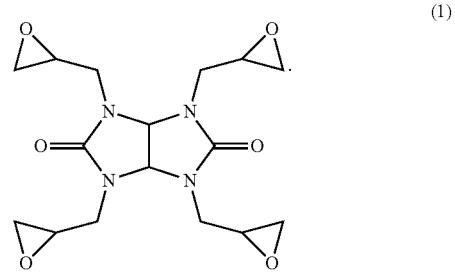

(1)

16 Claims, No Drawings

(51) Int. Cl.
  *H05K 1/02* (2006.01)
  *H05K 1/03* (2006.01)
  *C08J 5/18* (2006.01)
  *H01L 23/29* (2006.01)
  *H01B 1/20* (2006.01)
  *H05K 1/09* (2006.01)

(56) References Cited

FOREIGN PATENT DOCUMENTS

| | | | |
|---|---|---|---|
| DE | 1932305 | A1 | 3/1970 |
| EP | 0033503 | A2 | 8/1981 |
| EP | 0050939 | A1 | 5/1982 |
| JP | 56-122313 | A | 9/1981 |
| JP | 67-168956 | A | 10/1982 |
| JP | 11-171887 | A | 6/1999 |
| JP | 2010-224533 | A | 10/2010 |
| JP | 2011-89038 | A | 5/2011 |
| JP | 2014-24927 | A | 2/2014 |
| JP | 2014-185221 | A | 10/2014 |
| JP | 2015-54856 | A | 3/2015 |
| JP | 2015-116813 | A | 6/2015 |
| JP | 2015-117361 | A | 6/2015 |
| JP | 2015-117363 | A | 6/2015 |
| JP | 2015-120885 | A | 7/2015 |
| JP | 2015-120889 | A | 7/2015 |
| JP | 2015-120890 | A | 7/2015 |
| JP | 2015-121775 | A | 7/2015 |
| JP | 2015-194748 | A | 11/2015 |
| WO | 2015/076399 | A1 | 5/2015 |
| WO | 2015/163352 | A1 | 10/2015 |

OTHER PUBLICATIONS

Computer-generated English-language translation of DE1932305 A1.*
Computer-generated English-language translation of JP2015-120885 A (Jul. 2, 2015).*
International Search Report and Written Opinion, International Patent Application No. PCT/JP2016/052422, dated Mar. 29, 2016, with translation of International Search Report (10 pages).
Office Action, Chinese Patent Application No. 201680010463.3, dated Feb. 28, 2019, with machine translation (11 pages).
Office Action, Taiwanese Patent Application No. 105106690, dated Jul. 8, 2019 (4 pages).

* cited by examiner

THERMAL EXPANDABILITY ADJUSTER, USE AS THERMAL EXPANDABILITY ADJUSTER, THERMOSET RESIN COMPOSITION, INSULATING MATERIAL, SEALING MATERIAL AND CONDUCTIVE PASTE EACH CONTAINING THERMOSET RESIN COMPOSITION, CURED PRODUCTS, PREPREG AND MEMBER OBTAINED BY CURING THERMOSET RESIN COMPOSITION OF PREPREG, METHOD OF ADJUSTING THERMAL EXPANSION RATE, AND MEMBER MANUFACTURED USING METHOD OF ADJUSTING

TECHNICAL FIELD

The present invention relates to a thermal expandability adjuster, a use as a thermal expandability adjuster, a thermoset resin composition, an insulating material, sealing material and conductive paste each containing the thermoset resin composition, a cured product obtained by curing the thermoset resin composition, a substrate material having the thermoset resin composition, a prepreg obtained by impregnating a base material with the thermoset resin composition, a member obtained by curing the thermoset resin composition of the prepreg, a method of adjusting a thermal expansion rate, and a member manufactured using the method of adjusting.

BACKGROUND ART

In various fields centered on the electric and electronic industries, along with seeking to sophisticate electronic devices, such as reduction in size, acquisition of multifunctionality, and speedup of communication rate, circuit substrates used in such electronic devices are required to have a further dense structure. To respond to such demands for a dense structure, multilayered circuit substrates are developed.

A multilayered circuit substrate is manufactured, for example, through forming a conductor on an electrically insulating layer that is laminated on an inner layer substrate comprising an electrically insulating layer and a conductive layer formed on the surface of the electrically insulating layer, and repeating formation of an electrically insulating layer and a conductor. To respond to demands for such multilayered circuit substrates, various thermoset resin compositions are proposed (Patent Literature 1 to 3).

Patent Literature 1 describes using a resin composition that contains a specific epoxy resin, a phenol resin, a maleimide compound, and an inorganic filler in order to solve a problem caused by a highly-filled inorganic filler.

Patent Literature 2 describes a resin composition that contains a specific epoxy resin, curing agent, and inorganic filler. This resin composition can be preferably used for formation of an insulating layer of a circuit substrate.

Paten Literature 3 describes that, in order to provide a prepreg and the like excellent in the low thermal expandability and warpage characteristics, a thermoset resin composition layer included in the prepreg is composed of a thermoset resin composition that contains a specific maleimide compound, a specific siloxane diamine, and an amine compound having a specific acidic substituent.

PRIOR ART LITERATURE

Patent Literature

[Patent Literature 1] JP2014-185221A
[Patent Literature 2] JP2011-89038A
[Patent Literature 3] JP2014-24927A

SUMMARY OF THE INVENTION

Problems to be Solved by the Invention

The thermoset resin compositions disclosed in Patent Literature 1 to 3 each use an inorganic filler in order to reduce the linear thermal expansion coefficient. However, compounding an inorganic filler may cause deterioration in easy molding (referred also to as "moldability," hereinafter) of the thermoset resin composition.

Patent Literature 3 describes using a specific thermoset resin composition to reduce the linear thermal expansion rate or coefficient. When the thermoset resin composition described in Patent Literature 3 is used, however, a base material is impregnated with the thermoset resin composition. Thus, the disclosure of Patent Literature 3 is not for reducing the linear thermal expansion coefficient of a cured product that consists only of the thermoset resin composition.

Objects of the present invention include providing a thermal expandability adjuster that can reduce the linear thermal expansion coefficient of a cured product obtained by curing a thermoset resin composition, providing a use as a thermal expandability adjuster, providing a thermoset resin composition, providing a sealing material and conductive paste each containing the thermoset resin composition, providing a cured product obtained by curing the thermoset resin composition, providing a substrate material having the thermoset resin composition, providing a prepreg obtained by impregnating a base material with the thermoset resin composition, providing a member obtained by curing the thermoset resin composition of the prepreg, providing a method of adjusting a thermal expansion rate, and providing a member manufactured using the method of adjusting.

Means for Solving the Problems

The present invention provided for achieving the above objects is as follows.

<1> A thermal expandability adjuster that contains a glycoluril derivative compound represented by formula (1) below.

[Chemical Formula 1]

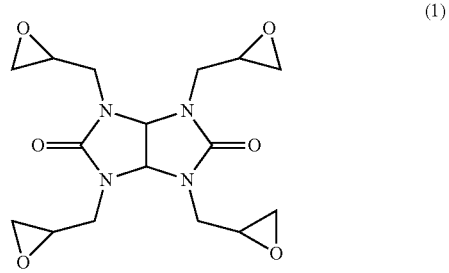

<2> A use of the glycoluril derivative compound represented by the above formula (1) as a thermal expandability adjuster.

<3> A thermoset resin composition that contains the thermal expandability adjuster as described in <1>.

<4> An insulating material that contains the thermoset resin composition as described in <3>.

<5> A sealing material that contains the thermoset resin composition as described in <3>.

<6> A conductive paste that contains the thermoset resin composition as described in <3>.

<7> A cured product obtained by curing the thermoset resin composition as described in <3>.

<8> The cured product as described in <7> having a linear thermal expansion coefficient of 40 ppm/° C. or less.

<9> The cured product as described in <7> having a glass transition temperature of 180° C. or higher.

<10> A substrate material having the thermoset resin composition as described in <3>.

<11> A prepreg obtained by impregnating a base material with the thermoset resin composition as described in <3>.

<12> A member obtained by curing the sealing material as described in <5>, the conductive paste as described in <6>, the thermoset resin composition of the substrate material as described in <10>, or the thermoset resin composition of the prepreg as described in <11>.

<13> A method of adjusting a linear thermal expansion coefficient of a member, comprising: a measurement step of measuring a linear thermal expansion coefficient of a member obtained by curing the thermoset resin composition as described in <3>; and an adjustment step of adjusting at least one of a usage of the thermoset resin composition and a content of a thermal expansion rate adjuster in the thermoset resin composition on the basis of the measured linear thermal expansion coefficient.

<14> The member as described in <12>, wherein a usage of the thermoset resin composition or a content of the thermal expansion rate adjuster is set using the method of adjusting a linear thermal expansion coefficient as described in <13>.

Effect of the Invention

According to the present invention, the linear thermal expansion coefficient of a cured product formed by curing a curable resin can be reduced. The difference of the linear thermal expansion coefficient can therefore be suppressed between a member formed of a cured product that constitutes a circuit substrate or the like and another member. The deformation of the circuit substrate or the like due to thermal stress can thus be suppressed.

BEST MODE(S) FOR CARRYING OUT THE INVENTION

Embodiments of the present invention will be described below.

The thermal expandability adjuster of the present invention contains a glycoluril derivative compound represented by formula (1) below.

[Chemical Formula 2]

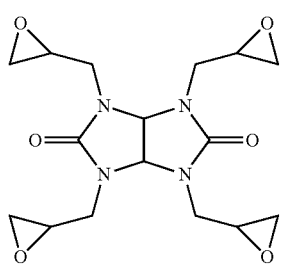

(1)

The present inventors have found that a cured product having a low linear thermal expansion coefficient can be obtained by curing a glycoluril derivative compound represented by formula (1) (which may also be referred to as a "glycoluril derivative compound," hereinafter) itself in a thermoset resin composition and that, when the glycoluril derivative compound is compounded in a thermoset resin composition, the linear thermal expansion coefficient of a cured product obtained by curing the thermoset resin composition is reduced. That is, the present inventors have newly discovered a property of the above-described glycoluril derivative compound and thereby conceived of the present invention which relates to a thermal expandability adjuster that contains the glycoluril derivative compound.

The thermoset resin composition of the present embodiment contains the glycoluril derivative compound and, therefore, a member having a low linear thermal expansion rate can be formed using a cured product obtained by curing the thermoset resin composition.

The thermal expandability adjuster of the present embodiment containing the glycoluril derivative compound may contain the glycoluril derivative compound as a part of the components or may consist only of the glycoluril derivative compound. Similarly, the thermoset resin composition containing a thermal expandability adjuster may contain the thermal expandability adjuster as a part of the components or may consist only of the thermal expandability adjuster.

The thermoset resin composition of the present embodiment contains a thermoset resin. Examples of the thermoset resin include an epoxy resin. Examples of the type of epoxy resin include, but are not limited to, an epoxy compound having two or more epoxy groups in one molecule, such as glycidyl ether-type epoxy resin, glycidyl ester-type epoxy resin, and glycidyl amine-type epoxy resin. Examples of the glycidyl ether-type epoxy resin include bisphenol A-type epoxy resin, bisphenol F-type epoxy resin, cresol novolac-type epoxy resin, phenol novolac-type epoxy resin, biphenyl-type epoxy resin, phenol biphenyl aralkyl-type epoxy resin, epoxidized product of aralkyl resin via xylylene bond such as phenol and naphthol, dicyclopentadiene-type epoxy resin, dihydroxynaphthalene-type epoxy resin, and triphenolmethane-type epoxy resin. These epoxy resins may be used alone or two or more types may also be used in combination.

When curing the epoxy resin, it is preferred to use a curing accelerator together therewith. Any known curing accelerator for curing an epoxy resin using a phenol-based curing agent can be used as the curing accelerator. Examples of the curing accelerator include a tertiary amine compound, a quaternary ammonium salt, imidazoles, a urea compound, a phosphine compound, and a phosphonium salt. More specific examples include a tertiary amine compound such as triethylamine, triethylenediamine, benzyldimethylamine, 2,4,6-tris(dimethylaminomethyl)phenol and 1,8-diazabicyclo(5,4,0)undecene-7; imidazoles such as 2-methylimidazole, 2,4-dimethylimidazole, 2-ethyl-4-methylimidazole, 2-phenylimidazole and 2-phenyl-4-methylimidazole; a urea compound such as 3-phenyl-1,1-dimethylurea, 3-(o-methylphenyl)-1,1-dimethylurea, 3-(p-methylphenyl)-1,1-dimethylurea, 1,1'-phenylenebis(3,3-dimethylurea) and 1,1'-(4-methyl-m-phenylene)-bis(3,3-dimethylurea); a phosphine compound such as triphenylphosphine, tributylphosphine, tri(p-methylphenyl)phosphine and tri(nonylphenyl)phosphine; and a phosphonium salt such as triphenyl phosphonio phenolate, tetraphenylphosphonium tetraphenylborate and tetraphenylphosphonium tetranaphthoic acid borate.

The glycoluril derivative compound serves not only as a thermal expansion adjuster for a cured product of the thermoset resin composition but also as an epoxy resin. The thermoset resin composition may contain the glycoluril derivative compound and other epoxy resins, etc. and may also contain only the glycoluril derivative compound.

By curing a thermoset resin composition that contains the glycoluril derivative compound, cured products having various shapes can be formed. When the thermoset resin composition of the present invention is used, therefore, a member having a predetermined linear thermal expansion coefficient can be easily formed.

By compounding the glycoluril derivative compound in a thermoset resin composition, a cured product having a small linear thermal expansion coefficient can be obtained. By compounding the above glycoluril derivative compound in a thermoset resin composition, a cured product having a linear thermal expansion coefficient of 40 ppm/° C. or less in an embodiment, or 25 ppm/° C. or less in another embodiment, can be obtained.

To reduce the linear thermal expansion coefficient of a cured product obtained by curing a thermoset resin composition, an inorganic filler has been conventionally used. The thermoset resin composition of the present embodiment contains a thermal expandability adjuster that contains the glycoluril derivative compound. It is therefore possible to reduce the amount of an inorganic filler necessary for reducing the linear thermal expansion coefficient of a cured product. In some cases, a cured product having a small linear thermal expansion coefficient can be formed without compounding an inorganic filler.

The glass transition temperature of a cured product may be preferably 180° C. or higher, more preferably 200° C. or higher, and further preferably 250° C. or higher.

The glass transition temperature within the above range allows a member formed of the cured product to have excellent rigidity and heat resistance. The glass transition temperature refers to a value that is obtained through measurement using a thermo-mechanical analysis (TMA) method when rising the temperature at a rate of 10° C. per minute from 40° C. to 300° C.

The compounding amount of the glycoluril derivative compound in the thermoset resin composition may be adjusted in accordance with the linear thermal expansion coefficient which is required for the cured product. To obtain effects as the thermal expandability adjuster, the compounding amount may be preferably 5 mass % or more and further preferably 20 mass % or more in 100 mass % of the thermoset resin composition.

The thermoset resin composition of the present embodiment may be preferably used as an insulating material. For example, it can be used as a sealing material (underfill material), conductive paste, molding material, various binders, mounting material, coating material, laminating material, etc.

As used herein, the sealing material refers to a material that seals a clearance gap thereby to prevent contact with external air of the components which constitute a circuit substrate. The sealing material also encompasses a solder resist that is used for the purpose of preventing solder from attaching to portions which do not require soldering.

As used herein, the conductive paste refers to a conductive paste-like material that is used as substitute for solder. In general, the conductive paste may be a resin composition obtained by dispersing low-melting-point metal particles in a thermoset resin composition.

The thermoset resin composition of the present embodiment can be used as a substrate material that has the thermoset resin composition and as a prepreg that is obtained by impregnating a base material with the thermoset resin composition. By curing the thermoset resin composition of these substrate material and prepreg, a member having a low linear thermal expansion coefficient can be manufactured. The obtained member may be used as a member that constitutes a flexible substrate or a rigid substrate.

As used herein, the substrate material having the thermoset resin composition refers to a material in which the thermoset resin composition is used as the raw material or constitutional element. Examples of such a substrate material include a film-like substrate material, such as an insulating resin sheet obtained by forming the thermoset resin composition into a film-like shape, and resin coated copper (RCC) comprising a resin that contains the thermoset resin composition.

As used herein, the prepreg refers to a material that is obtained through making the thermoset resin composition of the present embodiment into a varnish, impregnating a base material with the varnish, and heating or drying it into a partially-cured state. Examples of the base material to be used include an inorganic fiber, such as glass cloth and carbon fiber, and an organic fiber, such as polyamide, polyimide and polyester. These can be used alone or two or more can also be used in combination.

The thermoset resin composition of the present embodiment may contain a polymaleimide compound and a phenol compound in view of obtaining high heat resistance and excellent flame retardancy. The polymaleimide compound may preferably have two or more maleimide groups in one molecule. The phenol compound may preferably have at least two hydroxyl groups in a molecule. Examples of the polymaleimide compound and phenol compound to be used are, specifically, described in WO2012/057171.

Additives such as a curing agent, inorganic filler, coupling agent, release agent, colorant, flame retardant and stress reducer can be added, as necessary, to the thermoset resin composition of the present embodiment. Such additives may be used after being preliminarily reacted.

Examples of the inorganic filler include amorphous silica, crystalline silica, alumina, glass, calcium silicate, magnesite, clay, talc, mica, magnesia, and barium sulfate, among which amorphous silica, crystalline silica, and barium sulfate are particularly preferred. For increasing the compounding amount of the inorganic filler while maintaining excellent moldability, it is preferred to use a spherical inorganic filler having a wide particle size distribution that enables dense packing.

Examples of the coupling agent include a silane coupling agent, such as mercapto silane-based, vinyl silane-based, amino silane-based and epoxy silane-based coupling agents, and a titanium coupling agent. Examples of the releasing agent include carnauba wax and paraffin wax. Examples of the colorant include carbon black. Examples of the flame retardant include a phosphorous compound and metal hydroxide. Examples of the stress reducer include silicone rubber, modified nitrile rubber, modified butadiene rubber, and modified silicone oil.

The cured product obtained by curing the thermoset resin composition of the present embodiment uses the glycoluril derivative compound as the thermal expandability adjuster and, therefore, a member having a small content of an inorganic filler can be formed. For example, the content of an inorganic filler to 100 mass % of a member composed of the cured product can be 80 mass % or less in an embodiment or 50 mass % or less in another embodiment. By reducing the content of an inorganic filler in the thermoset resin composition, it is possible to suppress the deterioration of the formability due to the inorganic filler.

The present invention can also be carried out as a method of adjusting a linear thermal expansion coefficient (thermal expansion rate). An adjustment method of the present embodiment includes a measurement step of measuring a linear thermal expansion coefficient of a member obtained by curing the above-described thermoset resin composition of the present embodiment and an adjustment step of adjusting at least one of a usage of the thermoset resin composition and a content of a thermal expansion rate adjuster in the thermoset resin composition on the basis of the measured linear thermal expansion coefficient.

In the adjustment step, at least one of the usage of the thermoset resin composition and the content of the thermal expansion rate adjuster in the thermoset resin composition is adjusted on the basis of a measured value of the linear thermal expansion coefficient measured in the measurement step. This adjustment step allows the linear thermal expansion coefficient of the member to come close to a predetermined value. Thus, by repeating the measurement step and the adjustment step as needed, the linear thermal expansion coefficient can be adjusted and a member having a predetermined linear thermal expansion coefficient can be obtained.

According to the above-described method of adjusting the linear thermal expansion coefficient of a member, the usage of the thermoset resin composition or the content of the thermal expansion rate adjuster in the thermoset resin composition is adjusted in the adjustment step and a member composed of a cured product having a predetermined linear thermal expansion coefficient can be easily obtained.

Examples of the member composed of a cured product obtained by curing the thermoset resin composition include a resin film that is obtained by making the thermoset resin composition of the present embodiment into a varnish and heating and curing the varnish and a member that is obtained by heating and curing a prepreg. Some general-purpose solvent may be used for the resin component of the varnish, such as acetone, methyl ethyl ketone, dimethyl acetamide, and N-methyl-2-pyrrolidone. The compounding amount of the solvent is not particularly limited.

EXAMPLES

The present invention will be more specifically described below with reference to examples, but the present invention is not limited to these examples.
(Evaluation Methods)
Testing methods used in performance evaluation of the following examples and comparative examples are as follows.
(1) Glass Transition Temperature
Sepanium (release material obtained by treating an aluminum foil surface with a heat resistant release film) was disposed on each of upper and lower parts of one prepreg obtained in an example and the prepreg was heated at 4 MPa and 180-230° C. for 120 minutes for thermal curing. The glass transition temperature of the obtained specimen (sample) was measured. The measurement apparatus, measurement condition and the like were as follows.

Measurement equipment: "TMA8310evo" available from Rigaku Corporation
   Atmosphere: in nitrogen
   Measurement temperature: 30-300° C.
   Temperature rising rate: 10° C./min
   Load: 47 mN
(2) Linear Thermal Expansion Coefficient A resin film in a state of being manufactured was heated at 4 MPa and 180-230° C. for 120 minutes for thermal curing. With regard to a prepreg, the Sepanium was disposed on each of upper and lower parts of the prepreg, which was then heated at 4 MPa and 180-230° C. for 120 minutes for thermal curing. The linear thermal expansion coefficient of the molded sheet thus obtained was measured. The measurement apparatus, measurement condition and the like were as follows.

Measurement equipment: "TMA8310evo" available from Rigaku Corporation
   Atmosphere: in nitrogen
   Measurement temperature: 50-100° C.
   Temperature rising rate: 10° C./min
   Load: 47 mN
Details of raw materials used in the examples and comparative examples are as follows.
(1) Glycoluril derivative compound: 1,3,4,6-tetraglycidylglycoluril, TG-G (trade name, available from SHIKOKU CHEMICALS CORPORATION)
(2) Epoxy resin A: bisphenol epoxy resin, JER828EL (trade name, available from Mitsubishi Chemical Corporation)
Epoxy resin B: biphenyl aralkyl epoxy resin, NC3000 (trade name, available from Nippon Kayaku Co., Ltd.)
(3) Bismaleimide compound A: phenylmethane maleimide, BMI-2000 (trade name, available from Daiwakasei Industry Co., LTD)
(4) Bismaleimide compound B: 4,4'-diphenylmethane bismaleimide, BMI-1000 (trade name, available from Daiwakasei Industry Co., LTD)
(5) Phenol resin: naphthol aralkyl resin, SN-485 (trade name, available from NIPPON STEEL & SUMIKIN CHEMICAL CO., LTD.)
(6) Curing accelerator: U-CAT 3513N (trade name, available from Sanyo Chemical Industries, Ltd.)
(7) Reaction diluent: Neoallyl G (trade name, available from OSAKA SODA CO., LTD.)

Synthesis Example 1

(Synthesis of Varnish (I))

A round-bottomed flask provided with a stirrer, thermometer and condenser was charged with 270 mass parts of 4,4'-diphenylmethane bismaleimide (BMI-1000), 82 mass parts of naphthol aralkyl resin (SN-485), 221 mass parts of biphenyl aralkyl epoxy resin (NC3000), and 120 mass parts of methyl ethyl ketone (MEK), which were mixed and stirred for two hours after the internal temperature reached 80° C. Thereafter, 27 mass parts of a reactive diluent (allylglycidylether) and 12 mass parts of N-methyl-2-pyrrolidone (NMP) were added and a temperature of 80° C. was maintained for four hours.

Then, 28 mass parts of NMP were added and a temperature of 80° C. was further maintained for 18 hours. Then, 200 mass parts of MEK and 40 mass parts of NMP were added and stirred for two hours and there was thus obtained a varnish (I) of a modified polyimide resin composition in a state of being uniformly dissolved.

Example 1

A thin resin film was obtained through mixing 30 mass parts of TG-G and 70 mass parts of the varnish (I), adding 0.2 mass parts of U-CAT3513N as a curing accelerator, and curing them at a temperature of 150° C. to 230° C. for six hours. As a solvent for TG-G, 20 mass parts of methyl ethyl ketone was used.

Example 2

A thin resin film was obtained through the same method as in Example 1 except that the content of TG-G was 20 mass parts, the 70 mass parts of varnish (I) was substituted by a mixture of 78.4 mass parts of varnish (I) and 1.6 mass parts of JER828EL, and the content of methyl ethyl ketone as a solvent for TG-G was 15 mass parts.

Comparative Example 1

A thin resin film was obtained through the same method as in Example 1 except that 100 mass parts of varnish (I) was used as substitute for the 30 mass parts of TG-G and the 70 mass parts of varnish (I) and methyl ethyl ketone as a solvent for TG-G was not used.

Comparative Example 2

A thin resin film was obtained through the same method as in Example 1 except that 100 mass parts of JER828EL and 115.0 mass parts of SN-485 were used as substitute for the 30 mass parts of TG-G and the 70 mass parts of varnish (I).

Results of Examples 1 and 2 and Comparative Examples 1 and 2 are listed in the table below.

TABLE 1

|  | Example 1 | Example 2 | Comparative Example 1 | Comparative Example 2 |
|---|---|---|---|---|
| TG-G (mass parts) | 30 | 20 | — | — |
| Varnish (I) (mass parts) | 70 | 78.4 | 100 | — |
| SN-485 (mass parts) | — | — | — | 115 |
| JER828EL (mass parts) | — | 1.6 | — | 100 |
| Linear thermal expansion coefficient (ppm/° C.) | 10.3 | 8.0 | 49.9 | 61.9 |

The linear thermal expansion coefficient of the thin film as the cured product was smaller in Examples 1 and 2, in which TG-G was compounded in the thermoset resin composition, than in Comparative Examples 1 and 2, in which TG-G was not compounded. It has been found from these results that TG-G has a property of reducing the linear thermal expansion coefficient of the cured product and is useful as a thermal expansion adjuster for the thermoset resin composition.

Example 3

A thin resin film was obtained through adding 0.2 mass parts of U-CAT3513N as a curing accelerator to 100 mass parts of TG-G and curing them at a temperature of 150° C. to 230° C. for six hours.

Example 4

A thin resin film was obtained through the same method as in Example 3 except that the 100 mass parts of TG-G was substituted by 30 mass parts of TG-G and 70 mass parts of BMI-2000, 64 mass parts of SN485 was added, and 110 mass parts of dimethyl acetamide was used as a solvent for TG-G.

Example 5

A thin resin film was obtained through the same method as in Example 4 except that the content of SN485 was 47 mass parts.

Example 6

A thin resin film was obtained through the same method as in Example 4 except that the 70 mass parts of BMI-2000 was substituted by 70 mass parts of BMI-1000.

Example 7

A thin resin film was obtained through the same method as in Example 5 except that the 70 mass parts of BMI-2000 was substituted by 70 mass parts of BMI-1000.

TABLE 2

|  | Example 3 | Example 4 | Example 5 | Example 6 | Example 7 |
|---|---|---|---|---|---|
| TG-G (mass parts) | 100 | 30 | 30 | 30 | 30 |
| BMI-2000 (mass parts) | — | 70 | 70 | — | — |
| BMI-1000 (mass parts) | — | — | — | 70 | 70 |
| SN-485 (mass parts) | — | 64 | 47 | 64 | 47 |
| Linear thermal expansion coefficient (ppm/° C.) | −160 | 7.8 | −3.7 | 9.4 | 2.7 |

It has been found that, by using only TG-G as the thermoset resin in the thermoset resin composition and by using TG-G as the primary component of an epoxy resin, a thin resin film having a small linear thermal expansion coefficient can be obtained as a cured product of the thermoset resin composition.

Example 8

A resin varnish was prepared through adding 88.2 mass parts of the varnish (I), 1.8 mass parts of JER828EL, 7 mass parts of methyl ethyl ketone, 0.5 mass parts of U-CAT3513N as a curing accelerator, 0.01 mass parts of an additive (leveling agent), and 65 mass parts of an inorganic filler (spherical silica) to 10 mass parts of TG-G and uniformly stirring them.

Prepregs were each obtained through impregnating a glass cloth (2319 available from ASAHI KASEI E-materials Corp.) with the above resin varnish and drying it at a temperature of 230° C. for two hours. A copper-clad laminate was obtained through overlapping two of the above prepregs on each other, disposing copper foil of 18 μm as the outermost layer on each of the upper and lower parts, and molding them under a pressure of 2 to 4 MPa and a heating condition of 180° C. to 230° C. for 120 minutes.

Example 9

A copper-clad laminate was obtained through the same method as in Example 8 except that the 10 mass parts of TG-G, the 88.2 mass parts of varnish (I), the 1.8 mass parts of JER828EL, and the 7 mass parts of methyl ethyl ketone were substituted by 20 mass parts of TG-G, 78.4 mass parts of the varnish (I), 1.6 mass parts of JER828EL, and 13 mass parts of methyl ethyl ketone.

Example 10

A copper-clad laminate was obtained through the same method as in Example 8 except that the 10 mass parts of TG-G, the 88.2 mass parts of varnish (I), the 1.8 mass parts of JER828EL, and the 7 mass parts of methyl ethyl ketone were substituted by 30 mass parts of TG-G, 68.6 mass parts of the varnish (I), 1.4 mass parts of JER828EL, and 20 mass parts of methyl ethyl ketone.

For the prepregs of Examples 8 to 10 manufactured as the above, the glass transition temperature and the linear thermal expansion coefficient were measured using the methods described initially as the evaluation methods in the explanation of the examples. Results are listed in the table below.

TABLE 3

|  | Example 8 | Example 9 | Example 10 |
|---|---|---|---|
| TG-G (mass parts) | 10 | 20 | 30 |
| Varnish (I) (mass parts) | 88.2 | 78.4 | 68.6 |
| JER828EL (mass parts) | 1.8 | 1.6 | 1.4 |
| Impregnation ratio (mass %) | 52.1 | 52.1 | 52.1 |
| Linear thermal expansion coefficient (ppm/° C.) | 5.89 | 4.45 | 2.09 |
| Glass transition temperature (° C.) | 283 | — | 280 |

It has been found from the above results that, by increasing the compounding amount of TG-G, the cured product obtained by curing the thermoset resin composition of the prepreg exhibits a small linear thermal expansion coefficient.

INDUSTRIAL APPLICABILITY

The thermal expandability adjuster provided by the present invention is useful for adjusting the thermal expandability of the cured product of a thermoset resin composition to be used, for example, as a material for a circuit substrate and the like and obtaining a member having a desired linear thermal expansion coefficient.

The thermal expandability adjuster provided by the present invention is a composition that can give a cured product excellent in the low linear thermal expansion coefficient and a specific example is a thermoset resin composition that contains an epoxy resin.

The invention claimed is:
1. A thermoset resin composition, comprising:
a glycoluril derivative compound represented by formula (1)

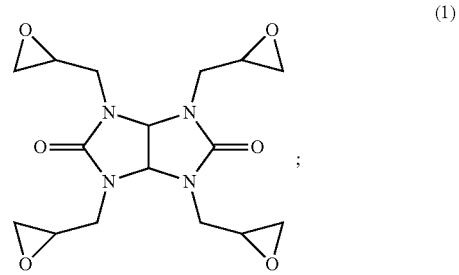 [SMILES: O=C1N(CC2CO2)C2C(N1CC1CO1)N(CC1CO1)C(=O)N2CC1CO1]

at least one bismaleimide compound;
at least one phenol resin; and
at least one epoxy resin other than the glycoluril derivative compound,
wherein the glycoluril derivative compound represented by the formula (1) is a thermal expansion rate adjuster.
2. An insulating material comprising the thermoset resin composition according to claim 1.
3. A sealing material comprising the thermoset resin composition according to claim 1.
4. A conductive paste comprising the thermoset resin composition according to claim 1.
5. A cured product obtained by curing the thermoset resin composition according to claim 1.
6. The cured product according to claim 5 having a linear thermal expansion coefficient in a range of 40 ppm/° C. or less.
7. The cured product according to claim 5 having a glass transition temperature in a range of 180° C. or higher.
8. A substrate material comprising the thermoset resin composition according to claim 1.
9. A prepreg obtained by impregnating a base material with the thermoset resin composition according to claim 1.
10. A member obtained by curing the sealing material according to claim 3.
11. A method of adjusting a linear thermal expansion coefficient of a member, comprising:
measuring a linear thermal expansion coefficient of a member obtained by curing the thermoset resin composition according to claim 1; and
adjusting a content of the thermal expansion rate adjuster in the thermoset resin composition on a basis of the measured linear thermal expansion coefficient.
12. A member obtained by curing the conductive paste according to claim 4.
13. A member obtained by curing the thermoset resin composition of the substrate material according to claim 8.
14. A member obtained by curing the thermoset resin composition of the prepreg according to claim 9.
15. The thermoset resin composition according to claim 1, wherein an amount of the glycoluril derivative compound in the thermoset resin composition is in a range of 20 mass % or more relative to the thermoset resin composition as 100 mass %.
16. The cured product according to claim 5, wherein an amount of an inorganic filler in the cured product is in a range of 50 mass % or less relative to the cured product as 100 mass %.

* * * * *